(12) United States Patent
Bausch et al.

(10) Patent No.: US 8,465,736 B2
(45) Date of Patent: Jun. 18, 2013

(54) GLUTADON

(75) Inventors: Michael Bausch, Berlin (DE); Wetzler Rainer, Berlin (DE); Christian Muller, Berlin (DE)

(73) Assignee: New Medical Enzymes AG, Berlin (DE)

( * ) Notice: Subject to any disclaimer, the term of this patent is extended or adjusted under 35 U.S.C. 154(b) by 776 days.

(21) Appl. No.: 12/300,209

(22) PCT Filed: May 10, 2007

(86) PCT No.: PCT/EP2007/004168
§ 371 (c)(1),
(2), (4) Date: Nov. 10, 2008

(87) PCT Pub. No.: WO2007/128588
PCT Pub. Date: Nov. 15, 2007

(65) Prior Publication Data
US 2009/0169537 A1    Jul. 2, 2009

(30) Foreign Application Priority Data

May 10, 2006   (EP) .................................... 06009696

(51) Int. Cl.
*A61K 38/48*   (2006.01)
(52) U.S. Cl.
USPC ...................................................... 424/94.6
(58) Field of Classification Search
USPC ...................................................... 424/94.6
See application file for complete search history.

(56) References Cited

U.S. PATENT DOCUMENTS 7,288,246 B2 * 10/2007 Miller .......................... 424/94.1
2006/0240414 A1 * 10/2006 Roberts et al. .................... 435/5

FOREIGN PATENT DOCUMENTS

WO   2004108153 A1   12/2004

OTHER PUBLICATIONS

McGregor, W.G. et al., "Glutaminase Enhances Therapeutic Effectiveness of Glutamine Antimetabolites Against Human and Murine Solid Tumors In Vivo". Proceeding of the annual meeting of the American Association for Cancer Research, vol. 30, Mar. 1989. p. 578, New Your, NY US.
Unger, C et al., "Phase I Dose Escalating Study of PEG-PGA and DON (GlutaDON): A New Amino Acid Depleting Anti Cancer Drug Approach", Journal of Clinical Oncology, vol. 22, No. 14S, 2004, p. 3175.
Unger, C et al., "Phase I Dose Escalating Study of PEG-PGA and DON: A New Amino Acid Depleting Anti Cancer Drug Approach", Journal of Clinical Oncology, vol. 23, No. 16S, Jun. 1, 2005, p. 3130.
Liebers, U. et al., Antitumorale Wirkung Von GlutaDON (R) Auf Zellimien Des Nichl-Kleinzelligen Lungenkarzinoms (NSCLC), 46, Kongreβ der Deutschen Gesellschaft für Pneumologie in Berlin, Mar. 16-19, 2005, p. 465.

* cited by examiner

*Primary Examiner* — Tekchand Saidha

(57)   ABSTRACT

The present invention relates to a pharmaceutical combination product for cancer therapy. The combination product comprises the two active ingredients glutaminase and 6-diazo-5-oxo-L-norleucine (DON). The invention further relates to the use of such a combination product for the treatment of cancers.

10 Claims, 1 Drawing Sheet

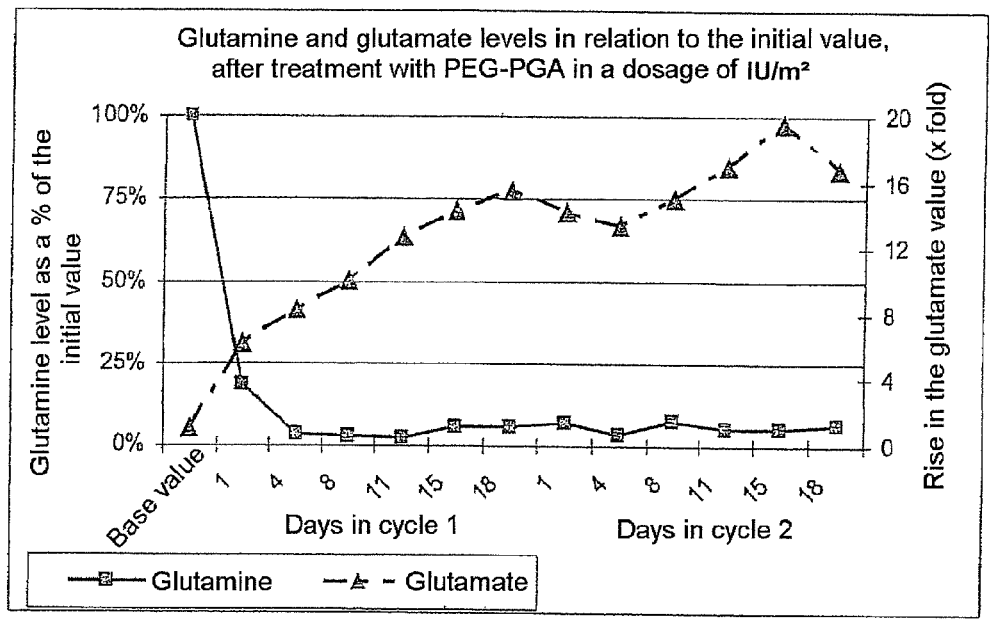

GLUTADON

FIELD OF THE INVENTION

The present invention relates to a pharmaceutical combination product for cancer therapy. The combination product comprises the two active ingredients glutaminase and 6-diazo-5-oxo-L-norleucine (DON). The invention also relates to the use of such a combination product for the treatment of cancers.

BACKGROUND OF THE INVENTION

The collective term "cancer" covers numerous different malignant diseases, which are characterized by the fact that the cells grow in an uncontrolled way, cell differentiation is absent, adjacent tissues are invaded, and metastases are formed. Almost every tissue can be the starting point of such a malignant disease.

Despite continuous progress, the current standard cancer treatments with antineoplastic active ingredients involve considerable detriments and risks for the patients. Owing to their unspecific antiproliferative effect and high dosage, these antineoplastic agents damage not only tumor cells but also rapidly growing healthy cells, such as for example mucous membranes, cells in the hemopoietic system (the bone marrow), and hair follicles. Treatment with antineoplastic agents is therefore generally associated with strong side effects, which detracts from the general well-being of the patients (acute side effects), cause irreversible damage to healthy tissue, and increase the risk of secondary tumors. Furthermore, tumors can build up resistance to active ingredients, which reduces the activity when a patient is treated with multiple dosages.

To obtain greater activities and reduce the development of resistance, a number of active ingredients are often combined and used for treatment at the same time (polychemotherapy). Despite this strategy, the problems described above have not been satisfactorily solved yet. It is therefore urgently required from the economic and medicinal viewpoint to find new and damage-free treatments for the fight against cancer.

A possible basis for the treatment of such malignant diseases is the reduction of the glutamine concentration in the bloodstream. Glutamine is the most common amino acid in the bloodstream and plays a decisive role as a source of nitrogen and energy, as well as a basic component of many synthetic processes in the cells. Owing to their vigorous growth, tumor cells are particularly dependent on glutamine in the bloodstream for use as a substrate in the biosynthesis of nucleotides and proteins, for energy generation, and for the production of metabolic intermediates in key positions of their metabolic pathways.

Numerous attempts were made in the 1980s to base cancer therapy on glutamine-cleaving enzymes or reactive glutamine analogs that deprive the tumor of its necessary glutamine. Roberts et al. showed that pseudomonas 7A glutaminase-asparaginase possesses an antineoplastic activity against numerous leukemic disorders in rodents, as well as against ascites tumors and certain solid tumors (DE 41 40 003 A1 and WO 94/13817 A1). In addition, it was found in animal experiments on athymic mice that the combination of glutamine analogs (e.g. 6-diazo-5-oxo-L-norleucine or DON) with glutaminase inhibits colon, breast and lung cancer in humans [W. McGregor and J. Roberts, *Proc. Anal. Assoc. Cancer Res.*, 30 (1989), p. 578]. It was also shown that treatment with glutaminase delayed the development of resistance to methotrexate [J. Roberts, F. A. Schmid and H. J. Rosenfeld, *Cancer Treat. Rep.*, 63 (1979), pp. 1045-1054].

However, the initially promising animal experiments did not lead to marketable medicaments, since therapeutical approaches using glutaminase or glutamine analogs (e.g. DON, acivicin) had to be discontinued initially, owing to severe toxic side effects (M. A. Medina: "Glutamine and Cancer", *The Journal of Nutrition*, vol. 131, No. 9, (2001), pp. 2539s-2542s). Despite the ideal concept of a glutamine depletion therapy, it has not been possible so far to achieve acceptance of a treatment based on proteins with a glutaminase activity.

However, since cancer still cannot be treated satisfactorily, it is of great medical and economic importance to find a way of using the promising concept of glutamine depletion therapy in future.

DESCRIPTION OF THE INVENTION

The problem the present invention is intended to solve therefore is to provide a preparation or rather a combination of preparations for the effective treatment of cancer, by using the active ingredients in concentrations that have little or no toxicity and cause little or no antibody formation while still being effective in the treatment of cancer.

It has now been found surprisingly that a combination of two preparations, comprising two active ingredients, namely a) glutaminase and b) 6-diazo-5-oxo-L-norleucine (DON) makes it possible to solve this problem if the active ingredient 6-diazo-5-oxo-L-norleucine is used in a dosage of from 50 to 300 mg/m$^2$, based on a recipient.

The invention therefore relates to a pharmaceutical combination product for cancer therapy, which combination product comprises the active ingredients a) glutaminase and b) 6-diazo-5-oxo-L-norleucine (DON), where active ingredient b) is present in a dosage of from 50 to 300 mg/m$^2$, based on a recipient.

According to the present invention, the term "glutaminase" denotes compounds that possess a glutaminase activity. The term "glutaminase" denotes in particular the proteins or enzymes glutaminase; glutaminase-asparaginase; glutaminase analogs; and derivatives and modifications, whether natural or synthetic. A therapeutically suitable glutaminase is preferably used according to the invention. Glutaminases that are therapeutically active cleave for example glutamine and/or asparagine. The therapeutically suitable glutaminases that are preferably used are those which have a sufficiently long half-life in the body to lower the level of glutamine and/or asparagines in the blood stream.

The use of glutaminase prepared by genetic engineering and/or pseudomonas glutaminase is preferred especially according to the invention. Glutaminases that can be used preferably according to the invention are described in WO 94/13817. Pseudomonas 7A glutaminase-asparaginase (PGA) is preferred in particular. In one of the embodiments, the compounds can be modified or provided with one or more protective substances. The modification or the use of protective substances protects glutaminase especially from host-mediated inactivation.

In a preferred embodiment, the protective substance for modification comprises an active carbohydrate, described in PCT/EP2003/004790.

Glutaminase can be modified with two or more different groups simultaneously.

The use of glutaminases modified with a straight-chain or branched polyalkylene glycol is particularly preferred according to the invention. Glutaminase can be modified with one or more polyalkylene glycol residues, especially polyethylene glycol residues. Glutaminase pegylated with 1-15 polyalkylene glycol residues, preferably with 1-5 polyalkylene glycol residues is preferred. The molecular weight of each polyalkylene glycol chain is preferably from 130 to 1,000,000 g/mol, more preferably from 500 to 100,000 g/mol, most preferably from 1,000 to 10,000 g/mol. Examples of preferred polyalkylene glycols include polyethylene glycols or polypropylene glycols, polyethylene glycols being preferred in particular. Glutaminase can be modified with a polyalkylene glycol according to the invention by any of the methods known to the expert in this connection.

Pseudomonas 7A glutaminase-asparaginase that is modified with polyethylene glycol and which is preferably used according to the invention is denoted here as PEG-PGA.

Polyethylene glycol is a hydrophilic polymer. It is known to have a low toxicity and a high biocompatibility. Conjugates formed by the activated polymer PEG and proteins and enzymes have been found to have a prolonged half-life in vivo, a reduced toxicity and a reduced renal elimination. In addition, the conjugates modified in this way have a high solubility in aqueous systems. The uses of pegylated systems are reviewed in N. K. Jain et al.: Pharmacy 2002, 57, pp. 5-29, entitled "PEGnology: A Review of the PEG-ylated Systems".

Polyalkoxylated polyols, such as for example monomethoxypolyethylene glycols (MPEG) or ethoxylated triethanolamine (TEA (EO)) can also be used for modifying glutaminase according to the invention.

In comparison with glutaminases used in the prior art, the pegylated glutaminase PEG-PGA, whose use is especially preferred according to the invention, has little or no neurotoxicity and hardly causes any nausea or vomiting in a recipient.

In the past, patients were treated with up to 20,000 IU/m² of glutaminases daily according to the prior art, but it lead to severe side effects (especially nausea, vomiting and neurotoxicity).

In the GlutaDON® study, PEG-PGA was found suitable for reducing the glutamine level to below 10% of the initial value and to keep it at that level (see Example 2) when used in a dosage of 120 IU/m² twice a week.

The second active ingredient in the combination product according to the invention is 6-diazo-5-oxo-L-norleucine (DON), which is an antimetabolite for glutamine.

An antimetabolite is a compound that only differs slightly from a physiologic compound in its chemical and/or structural characteristics. An antimetabolite is introduced into the metabolism instead of the physiologic compound in order to block or change the latter.

DON irreversibly inhibits numerous enzymes needed for DNA replication, protein synthesis and energy generation. This gives rise to a therapeutically utilized disruption of the metabolism of the tumor cell to be treated. Without being bound to this theory, the basis of the high activity of the glutamine antimetabolite 6-diazo-5-oxo-L-norleucine (DON) in combination with glutaminase is that the available glutamine level in the recipient is first reduced by the enzyme glutaminase to a low value, preferably to below 30% of the initial value, more preferably to below 10% of the initial value, still more preferably to below 5% of the initial value, and most preferably to below 1% of the initial value (always referring to weight). This reduction in the amount of glutamine in the recipient deprives the tumor to be treated of glutamine, producing an increased glutamine requirement.

Since after the administration of the antimetabolite DON the latter is then present in a large excess in comparison with glutamine, DON is intensively absorbed by the tumor to be treated and so displaces glutamine almost completely from the metabolic pathways of the tumor to be treated.

The action of DON is therefore increased synergistically by combination with glutaminase according to the invention.

Unlike in the case when DON is used by itself, the use of DON in combination with the therapeutically active glutaminase according to the invention hardly causes any side effects, such as nausea and vomiting. If used by itself, DON is further known to have an extremely low activity or none at all on solid tumors.

As the active ingredient a) glutaminase, preferably pseudomonas 7A glutaminase-asparaginase and more preferably pseudomonas 7A glutaminase-asparaginase modified with polyethylene glycol, preferably is present in the combination product at a concentration of from 20-400 IU/m² (international units per body surface of the recipient), preferably 40-300 IU/m², more preferably 50-200 IU/m², even more preferably 80-140 IU/m² and most preferably 115-125 IU/m² based on a recipient. These quantities refer to the amounts that are present in an administration unit.

The active ingredient a) is intended to be administered in the specified amount preferably three times a week to once every four weeks, more preferably twice a week to once every three weeks, and even more preferably twice a week to once a week.

The second active ingredient b), i.e. DON, is present in the combination with the active ingredient a) in an amount of 50-300 mg/m² (milligrams per body surface of the recipient), preferably 70-250 mg/m² more preferably 75-220 mg/m², even more preferably 80-200 mg/m², even more preferably 90-185 mg/m², even more preferably 100-170 mg/m², even more preferably 110-160 mg/m², even more preferably 120-150 mg/m² and most preferably 130-140 mg/m², based on a recipient. These quantities refer to the amounts that are present in an administration unit.

In a further particularly preferred embodiment, DON is present at a dosage of 170-190 mg/m².

The active ingredient b) is intended to be administered in the specified amount preferably four times a week to once every two weeks, more preferably three times a week to once a week and even more preferably twice a week.

When used by itself, DON competes with glutamine for absorption by the tumor cell (where glutamine is present in the recipient in a much larger amount), as a result of which the tumor cell takes up only a relatively small amount of DON even when it is administered in large dosages. When however DON is given in combination with glutaminase (and so there is a glutamine depletion), DON is present in the recipient in a much larger amount than glutamine, so that the tumor cell takes up a large amount of DON even if it is administered in comparatively small dosages, because then glutamine hardly competes any more.

Therefore, the DON dosage according to the invention, in combination with glutaminase, leads to a complete or at least extensive displacement of glutamine from the metabolism of the tumor.

In addition, healthy cells—unlike tumor cells—can manage without glutamine or can synthesize it as required.

Therefore, the result of the DON dosage according to the invention, in combination with glutaminase, is that the antimetabolite DON enters the tumor cell in a target-oriented way and is consequently markedly more effective in the treatment of a tumor than comparable or even considerably higher DON dosages when used by itself and in addition the incidence of side effects like nausea or vomiting is comparatively low.

In earlier clinical studies involving the use of DON by itself in dosages of up to 600 mg/m² (twice a week), DON only had a very modest action, and nausea and vomiting were reported to be dosage-limiting side effects. By contrast, in the Gluta- DON® study, carried out with the dosage range preferred according to the invention (up to 300 mg/m² and especially up to 185 mg/m²), a markedly better action was observed, without nausea and vomiting being found to be dosage-limiting side effects (see Example 1).

The combination product according to the invention can be administered in the form of a fixed combination, i.e. as a single pharmaceutical formulation comprising both active ingredients a) and b), or else it can be used in a free combination, where the active ingredients a) and b) are applied in separate pharmaceutical formulations, simultaneously or successively.

In a preferred embodiment of the invention, the active ingredients a), i.e. glutaminase, and b), i.e. DON, are present in two separate administration units, namely A), which contains the active ingredient a), and B), which contains the active ingredient b). The use of the glutaminase-containing administration unit A) reduces the glutamine level in the recipient to below 30% of the initial value, preferably to below 10% of the initial value, more preferably to below 5% of the initial value, and most preferably to below 1% of the initial value (always referring to weight) at the beginning of the treatment, before the administration unit B), which contains the antimetabolite DON, is administered to the recipient.

When there are two administration units A) and B), they can be formulated independently both as a liquid, both as a solid or one as a solid and one as a liquid.

If the active ingredients are solids, the active ingredients can be made into solid pharmaceutical preparations by the usual processes, for example by mixing the two active ingredients together and converting the mixture for example into tablets with the usual carriers and excipients. It is also possible, however, to supply the two active ingredients separately in one commercial packaging unit, wherein the packaging unit comprises both active ingredients but in separate pharmaceutical formulations.

In a preferred embodiment according to the invention, the active ingredients are supplied in the form of injection or infusion solutions. The injection or infusion solutions can be optionally applied separately from each other.

In the case of a parenteral dosage form, the active ingredients can be present in the original form, possibly together with the usual pharmaceutical excipients (for example in the lyophilized form), and then reconstituted or solubilized by the addition of pharmaceutically customary injection or infusion media.

The pharmaceutical preparations are applied in liquid or solid form in the case of enteral or parenteral application. All the usual application forms are possible here, for example tablets, capsules, sugarcoated tablets, syrups, solutions and suspensions. The injection medium is preferably water, containing the usual additives employed in injection solutions, such as stabilizers, solubilizers and buffers. Additives of this kind include tartrate and citrate buffers, ethanol, complexants such as ethylenediaminetetraacetic acid and its non-toxic salts, as well as high-molecular polymers, such as liquid polyethylene oxide for viscosity adjustment. The liquid carriers for injection solutions must be sterile, and they are preferably supplied in ampules. Solid carriers are for example starch, lactose, silica, higher molecular fatty acids such as stearic acid, gelatine, agar, calcium phosphate, magnesium stearate, animal and vegetable fats, and high-molecular solid polymers like polyethylene glycols. Preparations suitable for oral administration may contain flavors and sweeteners, if desired.

The present invention also relates to the use of a) glutaminase and b) DON for the preparation of a pharmaceutical combination product for the treatment of cancer. The preferred embodiments for this are as described hereinabove.

In a preferred embodiment, the administration unit B) is administered after the administration unit A). It is particularly preferred in this case to administer the administration unit B) after the administration unit A), when the glutamine level in the recipient has been reduced by the action of glutaminase present in administration unit A): to below 30%, preferably to below 10%, more preferably to below 5% and most preferably to below 1% of the initial glutamine level in the recipient (always referring to weight).

In a preferred embodiment, the administration unit B) is therefore administered from 1 minute up to 10 days, especially up to 10 hours, preferably from 10 minutes up to 4 hours and most preferably from 30 minutes up to 2 hours after the administration unit A). Another possibility is to administer a number of administration units A) after the administration of administration unit B).

It is preferable to administer one or both of the administration units A) and B) by the intravenous route. It is especially preferred to administer both administration units A) and B) intravenously.

The combination product is administered to a recipient especially once to three times a week and preferably twice a week.

In a preferred embodiment, the combination product is administered in a three-week cycle, but cycles of 1, 2, 4, 5, and 6 weeks or longer cycles are also possible, provided that no undesirable side effects appear.

When the glutamine level has been reduced, it is sufficient to administer the glutaminase once a week, especially as PEG-PGA preferably in a dosage of 115-125 IU/m², in order to keep the blood glutamine level at the reduced value.

The glutaminase administration, especially the administration of PEG-PGA, can be postponed or its dosage changed during a cycle in the case of for example too high a glutamate level, too high an ammonia level, rare allergic reactions, and the formation of antibodies to PEG-PGA, respectively.

It is generally possible to vary, within the range specified above, the concentrations of both active ingredients a) and b) in the combination product or in the administration units A) and B) according to several factors, such as the mode of administration, the species to be treated, sex, age and individual state, as well as accompanying therapeutic measures and other therapeutic features. Accordingly, the concentrations used can also be varied during a cycle, depending e.g. on the occurrence of unexpected recipient-specific side effects.

The preferred treatment uses a three-week cycle, comprising six administrations of the active ingredient b), i.e. DON.

The individual administration units of DON can be varied during the cycle according to the recipient and any undesirable side effects. After the lowering of the glutamine level, DON can in principle be used in conjunction with any administration scheme, provided that no undesirable side effects occur.

The combination product according to the invention can be used for the treatment of cancer, preferably renal cancer, colon cancer, prostate cancer, ovarian cancer, lung cancer and breast cancer. The treatment of lung cancer and colon cancer is preferred in particular.

The combination product according to the invention can also be used for the simultaneous treatment of several types of cancer in a recipient. The recipient according to the invention is preferably a mammal, especially a human being.

In another embodiment of the invention, the combination product according to the invention is administered in combination with one or more antineoplastic agents. Antineoplastic agents in this context are substances that are suitable for damaging or destroying microorganisms, parasites or tumor cells, and are used for this purpose. Examples of antineoplastic agents comprise additional antimetabolites, e.g. folic acid antagonists, such as methotrexate and pemetrexed, nucleoside analogs, such as mercaptopurine, fluorouracil (5FU), capecitabine and others, mitosis inhibitors; certain vinca alkaloids (e.g. vincristine and vinblastine) and taxanes (e.g. paclitaxel); alkylating and crosslinking agents, e.g. nitrogen lost derivatives such as cyclophosphamide and ifosfamide, N-nitroso compounds, such as carmustine, ethyleneimine (aziridine) derivatives, such as thiotepa, methanesulfonates such as busulfan, platinum complexes such as cisplatin, oxaliplatin or carboplatin, furthermore procarbazine, melphalan and others; cytostatic antibiotics, e.g. anthracyclines (e.g. daunorubicin, doxorubicin), bleomycin and mitomycins (e.g. etaposide), as well as actinomycins, e.g. actinomycin D and mitoxantrone; hormones and hormone antagonists, e.g. (anti-)estrogen (e.g. tamoxifen), including aromatase inhibitors, such as formestane, gestagens and antiandrogens, such as e.g. flutamide.

The additional antineoplastic agents can be administered simultaneously with the combination product according to the invention or independently, as part of an accompanying treatment.

The invention will be further explained with the aid of the following examples and FIG. 1.

BRIEF DESCRIPTION OF THE DRAWINGS

FIG. 1 shows the level of glutamine and glutamate after treatment with PEG-PGA in a dosage of 120 IU/m$^2$.

EXAMPLES OF THE INVENTION

EXAMPLE 1

In a phase I/IIa clinical study (GlutaDON®), altogether 58 patients with advanced carcinomas were treated with the combination of the two active ingredients described herein. The patients received PEG-PGA in a dosage of 120 IU/m$^2$ twice a week by the intravenous route, the infusion lasting 15 minutes. The administration of PEG-PGA was followed after 2-4 hours by the intravenous application of DON in a concentration of 5-185 mg/m$^2$. The duration of the infusion was again 15 minutes.

Table 1 shows that 7 out of 10 patients (70%) benefited from DON given in a dosage of 105-185 mg/m$^2$ (high DON dosage), as opposed to only 13 patients out of 36 (36%) treated with DON in a dosage of 5-80 mg/m$^2$ (low DON dosage).

According to the internationally accepted RECIST criteria, the term "stabilization" means that the increase in the measurable tumor diameters was less than 20% six weeks or more after the screening, i.e. after the staging of the tumor before the first treatment.

According to the internationally accepted RECIST criteria, the term "progression" means that a growth of more than 20%, or a subjective progression, or new lesions were observed within six weeks.

TABLE 1

Number of patients: 58
Number of evaluable patients: 46

| Indication | High DON dosage (105-185 mg/m$^2$) | | Low DON dosage (5-80 mg/m$^2$) | |
| --- | --- | --- | --- | --- |
| | Stabilization | Progression | Stabilization | Progression |
| Kidney | 4 | 0 | 5 | 4 |
| Prostate | 2 | 1 | 1 | 1 |
| Ovary | 1 | 0 | 1 | 4 |
| Colon | 0 | 1 | 2 | 4 |
| Other | 0 | 1 | 4 | 10 |
| Total | 7 (70%) | 3 (30%) | 13 (36%) | 23 (64%) |

The success of chemotherapy depends to a large extent on the number of metastases and previous treatments. The number of systemic therapies these patients had received before was on average 3.9 in the high-dosage group (105-185 mg/m$^2$ of DON), which was significantly higher than in the low-dosage group. In addition, the number of lesions per patient was 3.5, which is also significantly higher than in the low-dosage group.

The use of the higher DON dosages within the range according to the invention therefore shows a better activity in cancer therapy than that observed in the case of the lower DON dosages in the therapeutic regime described herein. In addition, nausea and vomiting were not dose-limiting. Overall, the administration of the two active ingredients according to the invention showed a very good activity, with at the same time less side effects for the patients in comparison with the use of DON by itself.

EXAMPLE 2

In the GlutaDON® study, 58 patients were treated with PEG-PGA in a dosage of 120 IU/m$^2$ twice a week. The glutamine level was monitored over a period of 6 weeks to find out how it had changed from the initial value in each patient. Overall, the blood glutamine level remained below 10% of the initial value (mostly even below 5%) over the whole period. The glutaminase used (PEG-PGA) in the specified concentration (120 IU/m$^2$, twice a week) is therefore suitable for use in accordance with the invention.

The invention claimed is:

1. A combination product for cancer treatment, which combination product comprises the active ingredients
   a) glutaminase and
   b) 6-diazo-5-oxo-L-norleucine (DON),
   where active ingredient a) is present in a dosage of from 40 I.U./m$^2$ to 300 I.U./m$^2$ based on a recipient; and
   where active ingredient b) is present in a dosage of from 105 to 185 mg/m$^2$ based on a recipient, where in the glutaminase is a glutaminase asparaginase from *Pseudomonas* 7A.

2. The combination product as claimed in claim 1, characterized in that active ingredient a) is modified and/or provided with one or more protective substances.

3. The combination product as claimed in claim 1, characterized in that active ingredient a) is present in a concentration of from 50 I.U./m$^2$ to 200 I.U./m$^2$ (international units per body surface area of recipient), based on a recipient, in the combination product.

4. The combination product as claimed in claim 1, characterized in that active ingredient a) is intended for administration three times a week to once every four weeks.

5. The combination product as claimed in claim 1, characterized in that active ingredient b) is intended for administration four times a week to once every two weeks.

6. The combination product as claimed in claim 1, characterized in that active ingredients a) and b) are present in a conjoint administration unit.

7. The combination product as claimed in claim 6, characterized in that active ingredients a) and b) are present in two separate administration units
   A) comprising active ingredient a) and
   B) comprising active ingredient b).

8. The combination product as claimed in claim 7, characterized in that at least one administration unit is in injectable form.

9. The combination product as claimed in claim 7, characterized in that at least one administration unit is in intravenous form.

10. The combination product as claimed in claim 7, characterized in that at least one administration unit is in oral form.

\* \* \* \* \*